United States Patent [19]

Böcker et al.

[11] 4,092,089
[45] May 30, 1978

[54] APPARATUS FOR THE PREPARATION OF MELT-SPRAYED SPHERICAL PHENACETIN GRANULES

[75] Inventors: Ernst Böcker; Wolfgang Kracht; Roland Rupp, all of Leverkusen; Erhard Schellmann, Cologne; Viktor Trescher; Martin Ullrich, both of Leverkusen, all of Germany

[73] Assignee: Bayer Aktiengesellschaft, Germany

[21] Appl. No.: 798,447

[22] Filed: May 19, 1977

Related U.S. Application Data

[60] Continuation-in-part of Ser. No. 635,607, Nov. 26, 1975, abandoned, which is a division of Ser. No. 564,169, Apr. 1, 1975, abandoned.

[30] Foreign Application Priority Data

Apr. 6, 1974 Germany ............................. 2416904

[51] Int. Cl.² ............................................. B29C 23/00
[52] U.S. Cl. ........................................ 425/10; 264/14; 425/376 A; 425/378 R; 425/DIG. 230

[58] Field of Search ........... 425/10, 378 R, DIG. 230, 425/205, 376 A; 264/13, 14

[56] References Cited

U.S. PATENT DOCUMENTS

| 3,078,513 | 2/1963 | Levison et al. | 425/376 A |
| 3,202,731 | 8/1965 | Grevenstuk et al. | 264/14 X |
| 3,386,131 | 6/1968 | Vanzo | 425/378 X |
| 3,421,182 | 1/1969 | Colombo | 425/378 X |
| 3,887,692 | 6/1975 | Gilman | 264/14 X |

Primary Examiner—Robert L. Spicer, Jr.
Attorney, Agent, or Firm—Jacobs & Jacobs

[57] ABSTRACT

An apparatus for melt-spraying thermally sensitive material of low viscosity comprises a heatable multi-screw extruder having intermeshing, self-cleaning screws of specified clearance between the screws and between the screws and the extruder housing, a heatable pump for delivering molten material from the extruder to a heatable atomizer and a spray tank in which the atomizer is located for cooling and solidifying the melt-sprayed material.

5 Claims, 3 Drawing Figures

APPARATUS FOR THE PREPARATION OF MELT-SPRAYED SPHERICAL PHENACETIN GRANULES

CROSS-REFERENCE

The present application is a continuation-in-part of our copending application Ser. No. 635,607, filed Nov. 26, 1975, now abandoned, which is in turn a divisional of our application Ser. No. 564,169, filed Apr. 1, 1975, now abandoned.

DETAILED DESCRIPTION

The present invention relates to apparatus for melt-spraying materials that are thermally sensitive in the molten state, and more particularly to apparatus for melt-spraying phenacetin.

It is well known that molten organic materials can be converted into granules by passing the molten material through a single nozzle, twin nozzle, or spinning disc atomizer and allowing subsequent solidification in a gas or a liquid; see e.g. W. Boretzky, in "Fette-Seinfen-Anstrichmittel,"No. 4, 1967, pp. 263–268 and G. Matz "Kristallisation in der Verfahrenstechnik" Springer 1957, pp. 284–291. These processes are preferably carried out with materials which are not sensitive to heat. Thus, W. Boretzky reports that stearic acid, paraffins and synthetic resins can be granulated in this way.

This procedure is not suitable for heat-sensitive substances since these tend to discolor and decompose on heating to, or above, their melting points. Previously, it has been possible to process such substances in the melt phase without degradation only if suitable reducing agents were added. German Offenlegungsschrift No. 1,617,933 discloses for example that pharmaceutically active compounds can be fused without decomposition if mixed with reducing agents, such as aqueous hydrazine solutions or ammonium formate solutions.

In the case of medicaments, such as phenacetin, however, any such reducing agents which are used in the preparation of granules must be completely removed in order to meet purity requirements. The latter process is therefore disadvantageous in that pure active compound is contaminated in order to fuse it, and a further purification step is thus necessary.

It has now been unexpectedly found that thermally sensitive materials having a viscosity of from about 0.5 to about 500 centipoise in the molten state, can be melt-sprayed into granules without the need for a reducing agent, and without being discolored, decomposed or otherwise deleteriously affected by the melting process, by means of the apparatus of the invention. Accordingly, the present invention provides apparatus for melt-spraying a material that is thermally sensitive in the molten state and has a melt viscosity of from about 0.5 to about 500 cp., which comprises (a) a multi-screw extruder for melting said material comprising intermeshing, self-cleaning screws having a clearance between the intermeshing screw shafts and a clearance between the screws and the housing of the extruder in the range of from about $4 \times 10^{-3}$ to about $30 \times 10^{-3}$ times the outer diameter of the screws, and means for heating said extruder;

(b) a heatable pump means connected to said extruder for pumping molten material from said extruder;

(c) a spray tank means having means for passing a cooling fluid therethrough;

(d) a heatable atomizing means in said spray tank means and connected to said pump means for melt-spraying molten material into said spray tank means to form granules thereof; and (e) said pump means being operable to pump molten material from said extruder to said atomizing means, and said spray tank means being operable to solidify the atomized material therein.

The present invention represents an unusual combination of extrusion and melt-spraying techniques. Thus, for melt-spraying or atomizing, the molten material must have a low viscosity in order to be capable of being atomized, i.e. a viscosity of less than about 500 cp. On the other hand, extruders have been developed and used for processing of thermoplastic plastics and polymers that have a high viscosity in the molten state, i.e. a viscosity of from about 50,000 to about 50,000,000 cp. Molten materials of such high viscosity cannot be atomized to form spherical granules, since melt-spraying only results in the formation of filaments. In addition, materials having low melt viscosities, and hence capable of atomization to form granules from the melt, are normally melted in a vessel equipped with a stirrer, and not in an extruder.

The average melt viscosity of materials that are suitable for melt-spraying is about 250 cp., based on a range of from about 0.5 to 500 cp., whereas the average melt viscosity of materials that are normally extruded generally have an average melt viscosity of 25,000,000 cp., based on a range of from about 50,000 to about 50,000,000 cp. There is thus a difference of five orders of magnitude ($10^5$) between the melt viscosity of materials used in melt-spraying and those used in extrusion, which demonstrates quite dramatically that there is a difference in kind between these materials. Accordingly, the apparatus of the present invention, which is based on the extrusion of low melt viscosity materials prior to melt-spraying, combines almost diametrically opposite techniques to provide an unexpected advance in the art.

The present invention may be used to advantage for the production of granules by melt-spraying any thermally sensitive material having a melt viscosity of from about 0.5 to about 500 cp., such as phenacetin. For the purpose of illustration, the following description of the invention is in terms of the processing of phenacetin, but similarly advantageous results can be obtained when other thermally sensitive materials are processed.

It is distinctly surprising that the heat-sensitive phenacetin is not discolored or decomposed in a melting device having wall temperatures more than 100° C above the melting point, since according to German Offenlegungsschrift No. 1,617,933, phenacetin decomposes even near the melting point if no suitable reducing agent is present.

The manufacture of phenacetin granules according to the invention represents a technical advance since these granules can now be readily and simply prepared without the need to add chemical auxiliaries to protect the melt against discoloration or decomposition, thereby obviating the need to subsequently remove such auxiliaries from the melt.

The melting device used preferably is a heated, intermeshing and self-cleaning multi-screw extruder with a short product residence time and a narrow product residence time spectrum with minimum clearance between the screw crests and housing as well as between the intermeshing screw shafts. A twin screw, with both screws rotating in the same direction and with clearances of from about 4 × 10⁻³ to about 30 × 10⁻³, based on the outer diameter of the screws, is particularly suitable for non-destructive melting of the material. Such a twin screw extruder has high heat transfer coefficients because of its particularly intense mixing effect, and a small volume filled with product. Additionally, because of its self-cleaning kinematics, deviations from the mean product residence time, which in any case is very short, are only slight.

The intake zone of the melting extruder should preferably be cooled to prevent accumulation of difficult to handle pasty states of the material, formed by premature melting, from hindering the flow of the crystalline phenacetin powder in the hopper zone. This intake zone is followed, in the feed direction, by a sealed, externally heated, enclosed melting zone. Here, the powder is heated to the melting point under intense forced convection, and is then melted. If desired, the screw shafts themselves can also be heated, in addition to the external heating of the housing.

The twin screw extruder thus described makes it possible to use very large differences in temperature between the heating medium and the phenacetin or other substance to be melted, while insuring that the molten material exits from the extruder at temperatures which, on the average, are no more than about 2° to about 3° C above the melting point. The melt issuing from the screw extruder is fed, either directly or via an intermediate container, to a heated pump and is brought to the atomizing pressure by this pump. Any components of the apparatus located between the exit of the screw extruder and the atomizing device, as a precautionary measure, should only be heated to a few degrees above the melting point. The total residence time of the material in the molten phase should be not more than about 20 minutes.

The solidification of the atomized melt, e.g. phenacetin, takes place in a known manner in an inert gas, such as air, nitrogen, or carbon dioxide, or liquid, such as water. When solidified in a gas, the product is obtained in its final form, while when solidified in a liquid, it must be subsequently dried.

The spherical phenacetin granules thus obtained, in contrast to crystalline phenacetin, can be tableted directly. Thus after simple admixture with customary tableting auxiliaries, it can be molded on high output tableting presses to yield tablets having good mechanical properties.

The present invention is illustrated in terms of a preferred embodiment in the accompanying drawings, in which.

Figure 1:
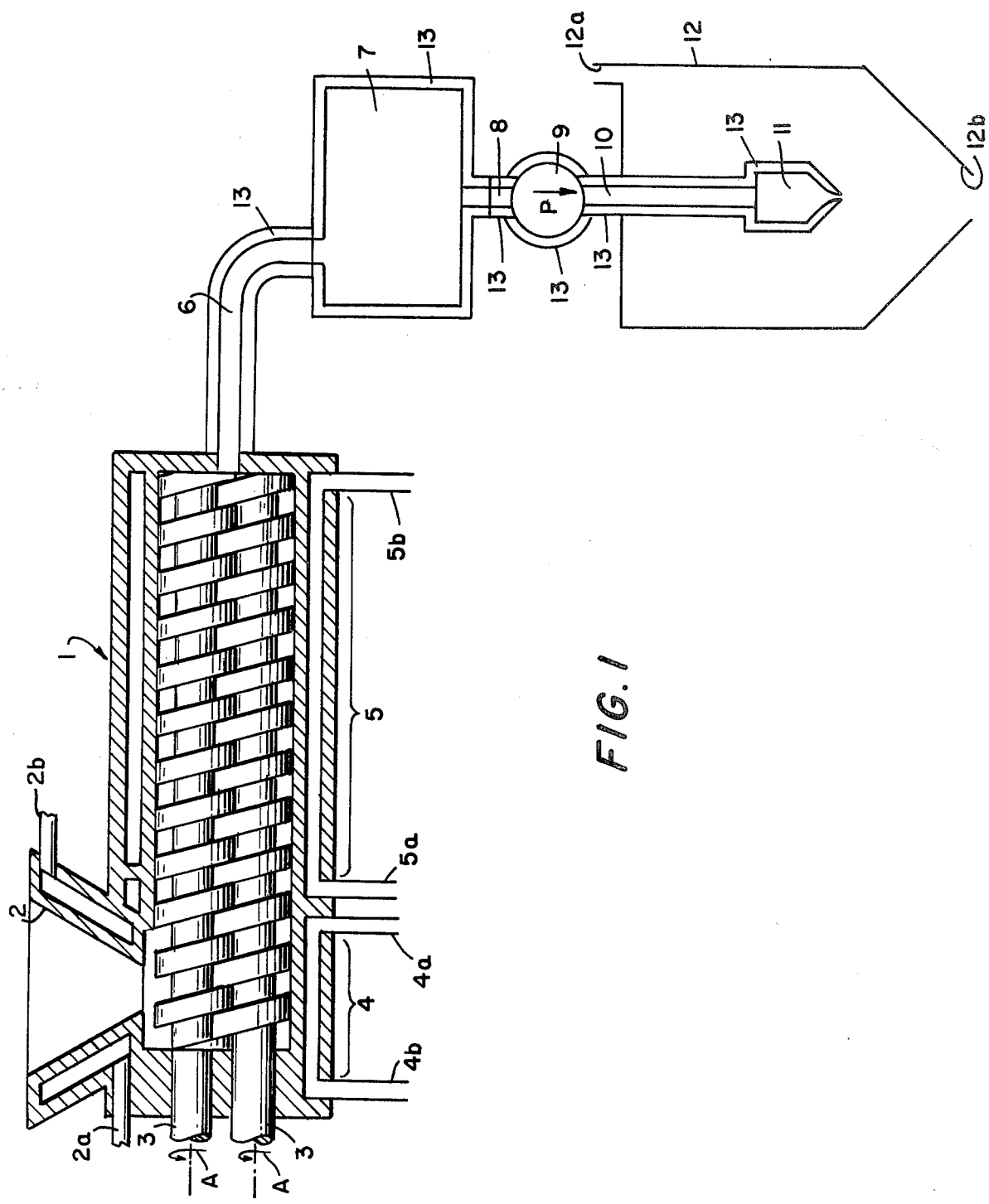
FIG. 1 is a schematic representation of the apparatus of the invention.

With reference to the FIG. 1 of the drawings, a twin screw extruder 1 has an inlet 2 into which the phenacetin or other thermally sensitive material is fed in any suitable form, such as granules or powder. The extruder 1 has twin screws 3 that rotate in the same direction, as shown by arrows A. Inlet 2 is provided with coolant via coolant entry 2a and exit 2b. Further, the extruder 1 has a cooling zone 4 at the beginning of screws 3 which is supplied by coolant via coolant inlet 4a and outlet 4b. Heating zone 5 follows the cooling zone 4 and is supplied by a suitable source of heat, such as heated oil, via inlet 5a and outlet 5b.

At the outlet of the extruder 1 is transfer pipe 6 which connects the extruder 1 to an intermediate container 7. Transfer pipe 8 connects the container 7 to pump 9. The outlet of pump 9 is connected to a transfer pipe 10, which terminates in a conventional atomizer 11 located in tank 12. Tank 12 is provided with cooling fluid inlet 12a and an outlet 12b. Each of the transfer pipes 6, 8, and 10 as well as the tank 7, pump 9 and atomizer 11 is provided with a heater 13, which may be a steam jacket, electrical heater or the like.

In operation, the screws 3 are caused to rotate and phenacetin or other thermally sensitive material is fed into extruder 1 via inlet 2. The inlet 2 and cooling zone 4 are cooled to avoid accumulation of pasty material at the inlet end of the screws 3. The phenacetin is then advanced by the screws 3 through the heating zone 5, wherein the phenacetin is melted under intense mixing action. Molten phenacetin is fed by the extruder 1 into container 7 via pipe 6, both of which are heated to maintain the phenacetin in a molten state. Molten phenacetin is pumped from container 7 via heated pipes 8 and 10 and heated pump 9 to atomizer 11, which acts to spray droplets of molten phenacetin into cooling tank 12. These droplets are cooled and solidified by the cooling fluid introduced into tank 12 via inlet 12a. Phenacetin granules exit from tank 12 along with the cooling fluid via outlet 12b.

Figure 2:
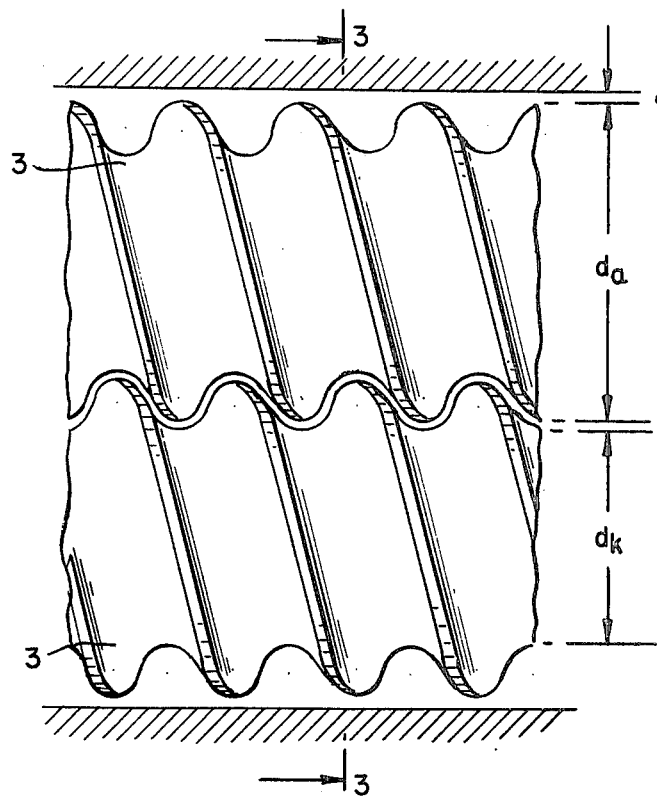
FIG. 2 is an enlarged detail view, in section, of the intermeshing screw shafts and showing the clearance between the screws and between the screws and the housing.
Figure 3:
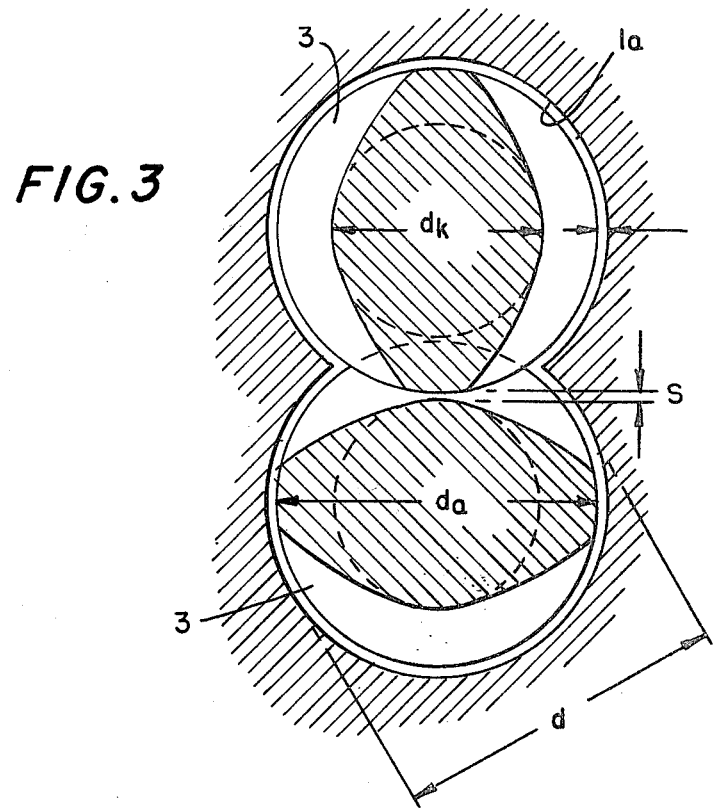
FIG. 3 is a view, in section, taken along lines 3—3 in FIG. 2 and showing the clearance between the intermeshing screw shafts and between the screws and the housing.

FIGS. 2 and 3 illustrate the tolerances between the two screws 3 and between each screw and the wall 1a of the extruder 1. Thus, each screw 3 has an outer diameter $d_a$ and an inner diameter $d_k$, while the inner diameter of the housing for each screw 3 is $d$. The clearance, δ, between each screw and the housing, and the clearance, s, between the two screws are each within the range of from about 4 × 10⁻³ to about 30 × 10⁻³ times $d_a$ The following examples illustrate the invention in terms of the production of spherical granules of phenacetin using the apparatus shown in the drawings.

EXAMPLE 1

Crystalline phenacetin was melted in an intermeshing twin screw extruder in which the screws rotate in the same direction, the outer diameter, $d_a$, of the screws being 31.6 mm and the inner diameter, $d_k$, being 16.8 mm with a screw length of 770 mm. The clearance, s, between the screws was 0.3 mm and the clearance, δ, between the screws and the housing was 0.2 mm. Based on the outer diameter, $d_a$, of the screws, it can be seen that s equals 9.49 × 10⁻³ times $d_a$ and δ equals 6.33 × 10⁻³ times $d_a$. The extruder was operated at wall temperatures of 190° C. The residence time in the extruder was 3.2 minutes and the throughput rate was 8 kg/hour. The melt at a viscosity of 1 cp. was fed by means of a piston pump to a vortex chamber nozzle and was thus atomized at about 140° C into air at about 20° C. The total residence time of the product under thermal stress was 13 minutes. The product was of requisite purity according to USP XVIII, and the following particle size distribution:

10% < 126 μm
50% < 242 μm

90% < 332 μm

It was very free-flowing and non-dusting.

EXAMPLE 2

Crystalline phenacetin was melted in the twin screw extruder described in Example 1, at wall temperatures of 210° C, using a residence time of 1.4 minutes in the extruder. The throughput rate was 18 kg/hour. By means of a piston pump the melt was fed to a vortex chamber nozzle and was thus atomized at about 140° C into air at about 20° C. The total residence time of the product under thermal stress was 6 minutes. The product conformed to the purity requirements of USP XVIII and had the following particle size distribution:

10% < 80 μm
50% < 160 μm
90% < 212 μm

EXAMPLE 3

Crystalline phenacetin was fused in the twin screw extruder described in Example 1, at wall temperatures of 270° C with a residence time of 1 minute in the extruder. The throughput rate was 26 kg/hour. By means of a piston pump, the melt was fed to a vortex chamber and was thus atomized at about 140° C into air at about 20° C. The total residence time of the product under thermal stress was 4 minutes. The solidified product had the requisite purity and the following particle size distribution:

10% < 91 μm
50% < 168 μm
90% < 247 μm

EXAMPLE 4

Crystalline phenacetin was melted in the twin screw described in Example 1, at wall temperatures of 210°, using a residence time of 1.5 minutes in the extruder. The throughput rate was 17 kg/hour. By means of a piston pump, the melt was fed to a vortex chamber nozzle and was thus atomized at about 142° C into air at about 20° C. The total residence time of the product under thermal stress was 6 minutes. The solidified and dried product had the requisite purity and the following particle size distribution:

10% < 38 μm
50% < 104 μm
90% < 230 μm

The spherical granules of phenacetin recovered from Examples 1-4 can be directly formed into tablets using high speed tablet presser, as contrasted to conventionally obtained phenacetin granules, which must be specially processed.

We claim:

1. Apparatus for melt-spraying a material that is thermally sensitive in the molten state and has a melt viscosity of from about 0.5 to about 500 cp., which comprises
   (a) a multi-screw extruder for melting said material comprising intermeshing, self-cleaning screws having a clearance between the intermeshing screw shafts and a clearance between the screws and the housing of the extruder in the range of from about $4 \times 10^{-3}$ to about $30 \times 10^{-3}$ times the outer diameter of the screws, and means for heating said extruder;
   (b) a heatable pump means connected to said extruder for pumping molten material from said extruder;
   (c) a spray tank means having means for passing a cooling fluid therethrough; and
   (d) a heatable atomizing means in said spray tank means and connected to said pump means for melt-spraying molten material into said spray tank means to form granules thereof;
   (e) said pump means being operable to pump molten material from said extruder to said atomizing means, and said spray tank means being operable to solidify the atomized material therein.

2. Apparatus according to claim 1, wherein said extruder is a twin screw extruder having both shafts rotatable in the same direction.

3. Apparatus according to claim 1, wherein said pump means is a piston pump means.

4. Apparatus according to claim 1, wherein a heatable, intermediate chamber means for storing molten material is located between said extruder and said pump means.

5. Apparatus according to claim 1, wherein said atomizing means is a vortex chamber nozzle.

* * * * *